United States Patent
Davila et al.

(10) Patent No.: US 6,245,100 B1
(45) Date of Patent: Jun. 12, 2001

(54) METHOD FOR MAKING A SELF-EXPANDING STENT-GRAFT

(75) Inventors: Luis A. Davila, Coral Springs; David Wilson, Ft Lauderdale, both of FL (US)

(73) Assignee: Cordis Corporation, Miami Lakes, FL (US)

( * ) Notice: Subject to any disclaimer, the term of this patent is extended or adjusted under 35 U.S.C. 154(b) by 0 days.

(21) Appl. No.: 09/494,861

(22) Filed: Feb. 1, 2000

(51) Int. Cl.$^7$ ............................. A61F 2/06; A61M 29/00
(52) U.S. Cl. .................................. 623/1.13; 606/198
(58) Field of Search ................. 606/194, 198, 606/200, 1, 108; 623/1.13, 1.18, 1.32, 1.12

(56) References Cited

U.S. PATENT DOCUMENTS

| | | |
|---|---|---|
| Re. 31,618 | 7/1984 | Mano . |
| 3,585,707 | 6/1971 | Stevens . |
| 4,187,390 | 2/1980 | Gore . |
| 4,604,762 | 8/1986 | Robinson . |
| 4,665,906 | 5/1987 | Jervis . |
| 4,705,517 | 11/1987 | DiPisa, Jr. . |
| 4,728,328 | 3/1988 | Hughes . |
| 4,731,073 | 3/1988 | Robinson . |
| 4,733,665 | 3/1988 | Palmaz . |
| 4,769,029 | 9/1988 | Patel . |
| 4,787,899 | 11/1988 | Lazarus . |
| 4,822,341 | 4/1989 | Colone . |
| 4,850,999 | 7/1989 | Planck . |
| 4,925,445 | 5/1990 | Sakamoto . |
| 4,955,899 | 9/1990 | Della Corna . |
| 5,045,072 | 9/1991 | Castillo . |
| 5,064,435 | 11/1991 | Porter . |
| 5,078,726 | 1/1992 | Kreamer . |
| 5,084,065 | 1/1992 | Weldon . |
| 5,100,422 | 3/1992 | Berguer . |
| 5,104,400 | 4/1992 | Berguer . |
| 5,123,917 | 6/1992 | Lee . |
| 5,151,105 | 9/1992 | Kwan-Gett . |
| 5,152,782 | 10/1992 | Kowligi . |
| 5,156,620 | 10/1992 | Pigott . |
| 5,163,951 | 11/1992 | Pinchuk . |
| 5,207,695 | 5/1993 | Trout, III . |
| 5,211,658 * | 5/1993 | Clouse ............................... 623/1.18 |
| 5,219,355 | 6/1993 | Parodi ................................. 606/191 |
| 5,236,447 | 8/1993 | Kubo ...................................... 623/1 |
| 5,246,452 | 9/1993 | Sinnott .................................... 623/1 |
| 5,254,107 | 10/1993 | Soltesz ................................ 604/282 |
| 5,258,027 | 11/1993 | Berghaus ................................ 623/9 |
| 5,282,860 | 2/1994 | Matsuno ............................... 623/12 |
| 5,306,294 | 4/1994 | Winston .................................. 623/1 |
| 5,321,109 | 6/1994 | Bosse .................................. 526/255 |
| 5,330,490 | 7/1994 | Wilk ................................... 606/153 |
| 5,330,500 | 7/1994 | Song . |
| 5,330,528 | 7/1994 | Lazim . |

(List continued on next page.)

FOREIGN PATENT DOCUMENTS

| | | |
|---|---|---|
| 0 686 379 | 12/1995 | (EP) . |
| 0 855 170 | 7/1998 | (EP) . |

(List continued on next page.)

Primary Examiner—William Lewis

(57) ABSTRACT

In accordance with the present invention, there is provided a method of making a stent-graft for insertion into target site within a vessel of a patient. The graft has a crimped state for delivery to the target site, and an expanded state for implantation therein. The method uses a self-expanding tubular elastic outer stent having a crimped and expanded state, and includes the step of expanding the outer stent to its expanded state. The method also uses a tubular flexible porous graft member and includes the step of inserting the graft member along an interior of the outer stent. The method also uses a self-expanding tubular elastic inner stent, and includes the step of crimping the outer stent to a diameter smaller than a diameter of the expanded outer stent. The method then continues by inserting the inner stent within an interior of the graft member, and expanding the inner stent such that the inner stent, the graft member and the outer stent are all abutting.

24 Claims, 12 Drawing Sheets

U.S. PATENT DOCUMENTS

| | | |
|---|---|---|
| 5,334,201 | 8/1994 | Cowan . |
| 5,366,473 | 11/1994 | Winston . |
| 5,380,328 | 1/1995 | Morgan . |
| 5,383,927 | 1/1995 | DeGoicoechea . |
| 5,453,235 | 9/1995 | Calcote . |
| 5,466,509 | 11/1995 | Kowligi . |
| 5,468,138 | 11/1995 | Bosse . |
| 5,512,229 | 4/1996 | Bosse . |
| 5,522,882 | 6/1996 | Gaterud . |
| 5,549,663 | 8/1996 | Cottone, Jr. . |
| 5,609,624 | 3/1997 | Kalis . |
| 5,628,786 | 5/1997 | Banas . |
| 5,628,788 | 5/1997 | Pinchuk . |
| 5,632,778 | 5/1997 | Goldstein . |
| 5,641,443 | 6/1997 | Cacpte . |
| 5,645,559 | 7/1997 | Hachtman . |
| 5,667,523 | 9/1997 | Bynon . |
| 5,674,241 | 10/1997 | Bley . |
| 5,681,345 | 10/1997 | Euteneuer . |
| 5,683,448 | 11/1997 | Cragg . |
| 5,700,285 | 12/1997 | Myers . |
| 5,723,003 | 3/1998 | Winston . |
| 5,728,131 * | 3/1998 | Frantzen et al. ............... 623/1.13 |
| 5,735,892 | 4/1998 | Myers . |
| 5,749,880 | 5/1998 | Banas . |
| 5,788,626 | 8/1998 | Thompson . |
| 5,810,870 | 9/1998 | Myers . |
| 5,824,043 | 10/1998 | Cottone, Jr. . |
| 5,824,046 | 10/1998 | Smith . |
| 5,824,054 | 10/1998 | Khosravi . |
| 5,827,327 | 10/1998 | McHaney . |
| 5,843,120 | 12/1998 | Israel . |
| 5,858,556 | 1/1999 | Eckert . |
| 5,916,264 | 6/1999 | Von Oepen . |
| 5,935,667 | 8/1999 | Calcote . |
| 5,980,565 | 11/1999 | Jayaraman . |

FOREIGN PATENT DOCUMENTS

| | | |
|---|---|---|
| 55-24095 | 2/1980 | (JP) . |
| 60-220030 | 11/1985 | (JP) . |
| 62-231657 | 10/1987 | (JP) . |
| 4-64367 | 2/1992 | (JP) . |
| 4-263852 | 9/1992 | (JP) . |
| 5-76603 | 3/1993 | (JP) . |
| 5-269199 | 10/1993 | (JP) . |
| 6-282730 | 10/1994 | (JP) . |
| 7-000529 | 1/1995 | (JP) . |
| 7-024072 | 1/1995 | (JP) . |
| 7-100210 | 4/1995 | (JP) . |
| 6-86827 | 6/1998 | (JP) . |
| 1680055 | 5/1988 | (RU) . |
| WO 97/24081 | 7/1997 | (WO) . |
| WO 98/53761 | 12/1998 | (WO) . |

* cited by examiner

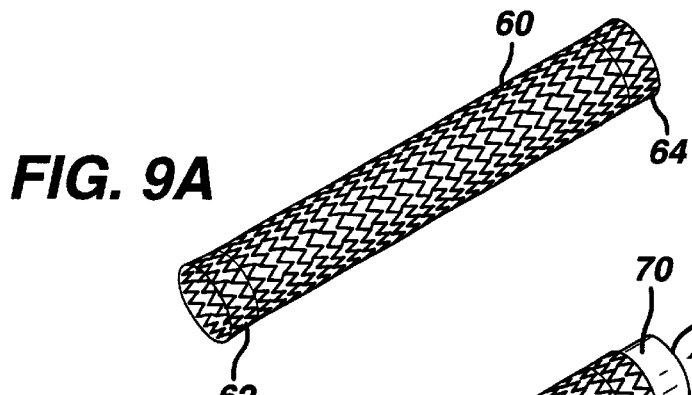
FIG. 9A
FIG. 9B
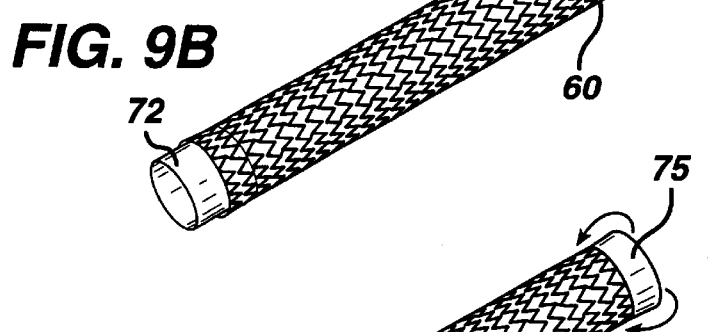
FIG. 9C
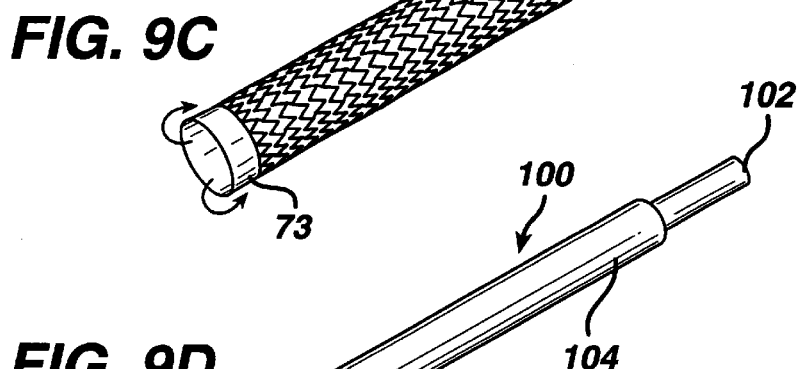
FIG. 9D
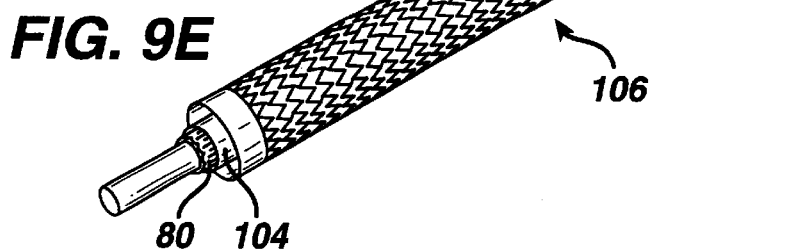
FIG. 9E

METHOD FOR MAKING A SELF-EXPANDING STENT-GRAFT

FIELD OF THE INVENTION

The present invention relates to expandable intraluminal stent-grafts, or covered stents, for use within a body passageway or duct which are particularly useful for repairing blood vessels or otherwise treating vascular disease. The present invention relates even further to such stent-grafts which are self-expanding.

BACKGROUND OF THE INVENTION

It is well known to employ various intravascular endoprostheses delivered percutaneously for the treatment of diseases of various body vessels. These types of endoprosthesis are commonly referred to as stents. A stent is a generally formed longitudinal tubular device of biocompatible material, such as stainless steel, having holes or slots cut therein so they can be radially expanded, by a balloon catheter or the like, within the vessel. Stents are useful in the treatment of stenosis, strictures or aneurysms in body vessels such as blood vessels. These devices are implanted within the vessel to reinforce collapsing, partially occluded, weakened or abnormally dilated sections of a vessel. Stents are typically employed after angioplasty of a blood vessel to prevent restenosis of the diseased vessel. While stents are most notably used in blood vessels, stents may also be implanted in other body vessels such as the urogenital tract and bile duct.

Stents generally include an open flexible configuration. This configuration allows the stent to be inserted through curved vessels. Furthermore, the stent configuration allows the stent to be configured in a radially compressed state for intraluminal catheter implantation. Once properly positioned adjacent the damaged vessel, the stent is radially expanded so as to support and reinforce the vessel. Radial expansion of the stent can be accomplished by inflation of a balloon attached to the catheter. Examples of various stent constructions are shown in U.S. Pat. No. 4,733,665 filed by Palmaz on Nov. 7, 1985, which is hereby incorporated herein by reference.

However, such balloon expandable stents are often impractical for use in some vessels such as the carotid artery. The carotid artery is easily accessible from the exterior of the human body, and is often visible by looking at ones neck. A patient having a balloon expandable stent made from stainless steel or the like, placed in their carotid artery might be susceptible to sever injury through day to day activity. A sufficient force placed on the patients neck, such as by falling, could cause the stent to collapse, resulting in injury to the patient. In order to prevent this, self expanding stents have been proposed for use in such vessels. Self expanding stents act like springs and will recover to their expanded or implanted configuration after being crushed.

Many self-expanding stents employ the use of alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable (the Af temperature). The shape of the metal during this heat treatment is the shape "remembered." The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape if unrestrained. If restrained, the metal will remain martensitic until the restraint is removed.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increases in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

Recently, there has been a desire to place a covering of biocompatible material over expandable stents. The covering for the stent can provide many benefits. For example, the covered stent could act as a graft. Intraluminal vascular grafts can be used to repair aneurysmal vessels, particularly aortic arteries, by inserting an intraluminal vascular graft within the aneurysmal vessel so that the prosthetic withstands the blood pressure forces responsible for creating the aneurysm. In addition, due to the open nature of uncovered stents there is a tendency for the stent to permit passage of material through the body of the stent. Such material may include excessive cell or tissue growth (intimal hyperplasia), thrombus formations and plaque in vascular situations and tumors in the bile or urogenital tract. These materials may have a tendency to block or otherwise re-occlude the open vessel. While covers would prevent material from passing through the stent wall, the covering itself must be sufficiently flexible so as to permit crimping of the stent for delivery, and subsequent deployment of the stent thereafter. Furthermore, the cover must be sufficiently attached to the stent that it will not detached during delivery and deployment.

In the past, in order to achieve a covered stent that has the necessary flexibility and attachment, most prior art covered stents have been balloon expandable covered stents. One example of this is shown in U.S. Pat. No. 5,667,523 issued to Bynon et al. on Sep. 16, 1997, which is hereby incorporated herein by reference. The Bynon et al. reference discloses a dual supported intraluminal graft comprising a biocompatible flexible layer, such as Polytetrafluroethylene (PTFE), sandwiched between two balloon expandable stents. The ends of the PTFE graft are folded back onto the outer surface of the second structural support, thereby forming flaps.

However, the covered stent disclosed in the Bynon reference, has many disadvantages when the balloon expandable stents are replaced with self-expanding stents. The PTFE graft layer disclosed therein is not attached to the outer stent. Its position is maintained only by the force of the inner stent pressing against the outer stent. Because the outward force exerted by a self-expanding stent is typically not large, the graft material could slip and move relative to the stents, which could cause the device not to function optimally. In addition, the Bynon et al. reference discloses that the PTFE graft is placed between the stents, when the stents are in their crimped condition. However, due to the nature of self-expanding stents, the graft material has to placed within the stents while the stents are in their fully expanded condition. This raises the possibility of damaging the stents when they are crimped for implantation. Damaging the PTFE material could also cause the device to not function optimally.

Therefore, there has been a need to have a self-expanding covered stent which overcomes the disadvantages of the prior art covered stents. There has also been a further need for a method of manufacturing a self-expanding covered stent which overcomes the disadvantages of prior art manufacturing methods. The present invention provides such a solution.

SUMMARY OF THE INVENTION

In accordance with the present invention, there is provided a method of making a stent-graft for insertion into a target site within a vessel of a patient. The graft has a crimped state for delivery to the target site, and an expanded state for implantation therein. The method uses a self-expanding tubular elastic outer stent having a crimped and expanded state, and includes the step of expanding the outer stent to its expanded state. The method also uses a tubular flexible porous graft member and includes the step of inserting the graft member along an interior of the outer stent. The method also uses a self-expanding tubular elastic inner stent, and includes the step of crimping the outer stent to a diameter smaller than a diameter of the expanded outer stent. The method then continues by inserting the inner stent within an interior of the graft member, and expanding the inner stent such that the inner stent, the graft member and the outer stent are all abutting.

BRIEF DESCRIPTION OF DRAWINGS

The foregoing and other aspects of the present invention will best be appreciated with reference to the detailed description of the invention in conjunction with the accompanying drawings, wherein:

FIGS. 9A–9K are perspective and partial perspective views showing a stent-graft in accordance with the present invention being manufactured in accordance with the steps shown in FIG. 8.

DETAILED DESCRIPTION OF THE INVENTION

Figure 6:
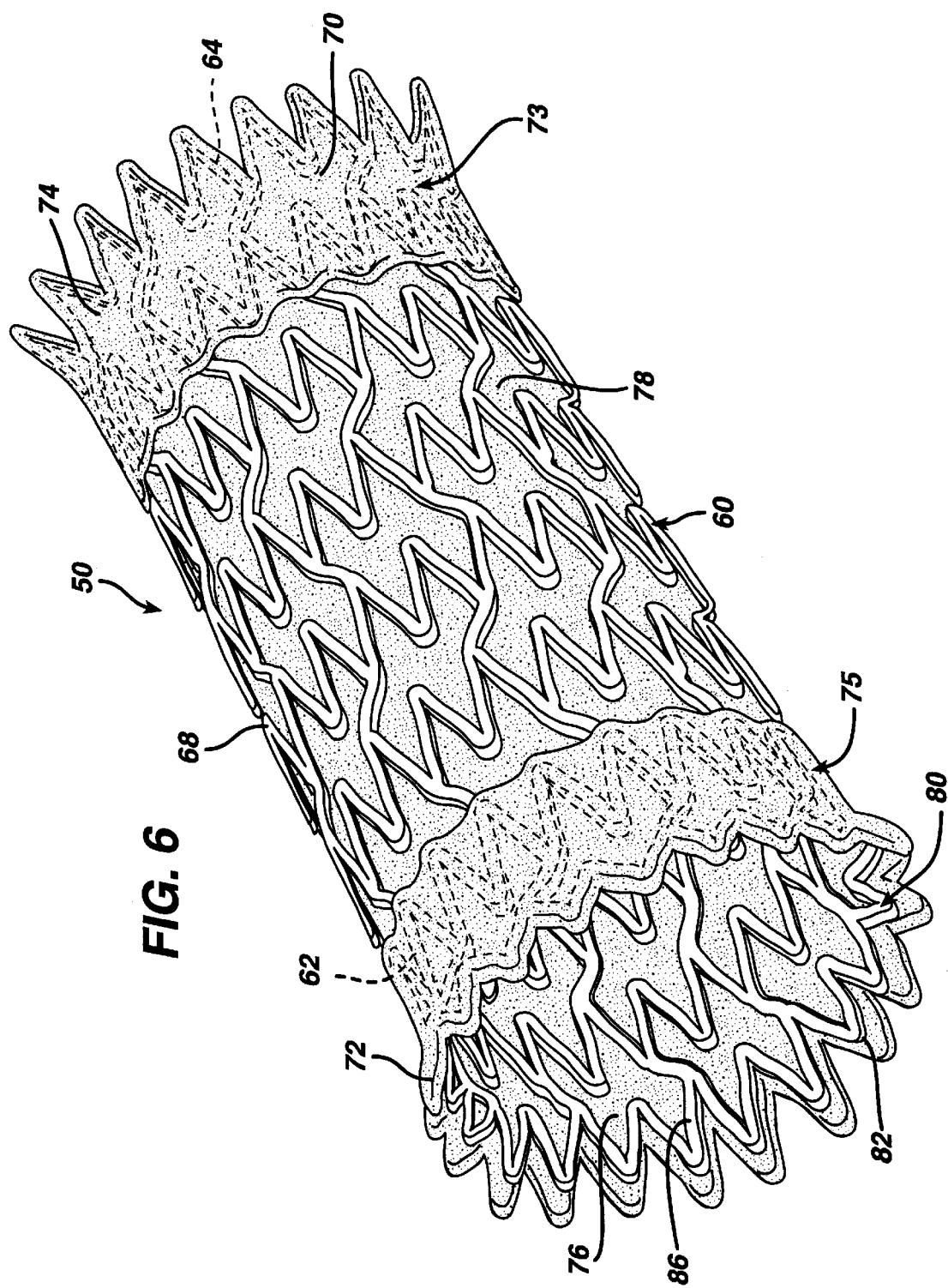
FIG. 6 is a partial perspective view of a stent graft made in accordance with the present invention, and showing such stent-graft in its expanded state.

Referring now to the figures wherein like numerals indicate the same element throughout the views, there is shown in FIG. 6 a stent-graft 50 made in accordance with the resent invention. Stent-graft 50 is designed for insertion into a target site within a vessel of a patient, to treat various vascular diseases. The stent-graft 50 has a crimped state, shown in FIGS. 1 and 2, for delivery to the target site, and an expanded state, shown in FIG. 6 for implantation within the vessel. Individual parts of the stent graft 50 will be described in detail below, however, a brief description of the overall device would be helpful in understanding the design.

Stent-graft 50 includes a self-expanding outer stent 60, which is a tubular member having a front end 62 and a back end 64. The stent 60 has an interior surface 66, which is not pointed out in FIG. 6 because it is obstructed, and an exterior surface 68. Stent 60 is preferably made from an elastic material. Stent-graft 50 further includes a tubular flexible porous graft member 70, preferably expanded PTFE, extending along the interior of the outer stent. Graft member 70 has a front end 72, a back end 74, an interior surface 76 and an exterior surface 78. As seen from the drawings, the front and back ends of the graft member 72 and 74 are folded over and bonded to the front and back ends of the outer stent 62 and 64 to form cuffs 73 and 75. Graft member 50 also includes a self-expanding inner stent 80, similar to stent 60. Self-expanding inner stent 80 is a tubular member having a front end 82, a back end 84, which is not pointed out in FIG. 6 because it is obstructed, an interior surface 86 and an exterior surface 88, which is not pointed out in FIG. 6 because it is obstructed. Stent 80 is preferably made from an elastic material. Inner stent 80 is disposed within the interior of the graft member such that the inner stent, the graft member and the outer stent are all abutting, as shown in FIG. 6.

Figure 3:
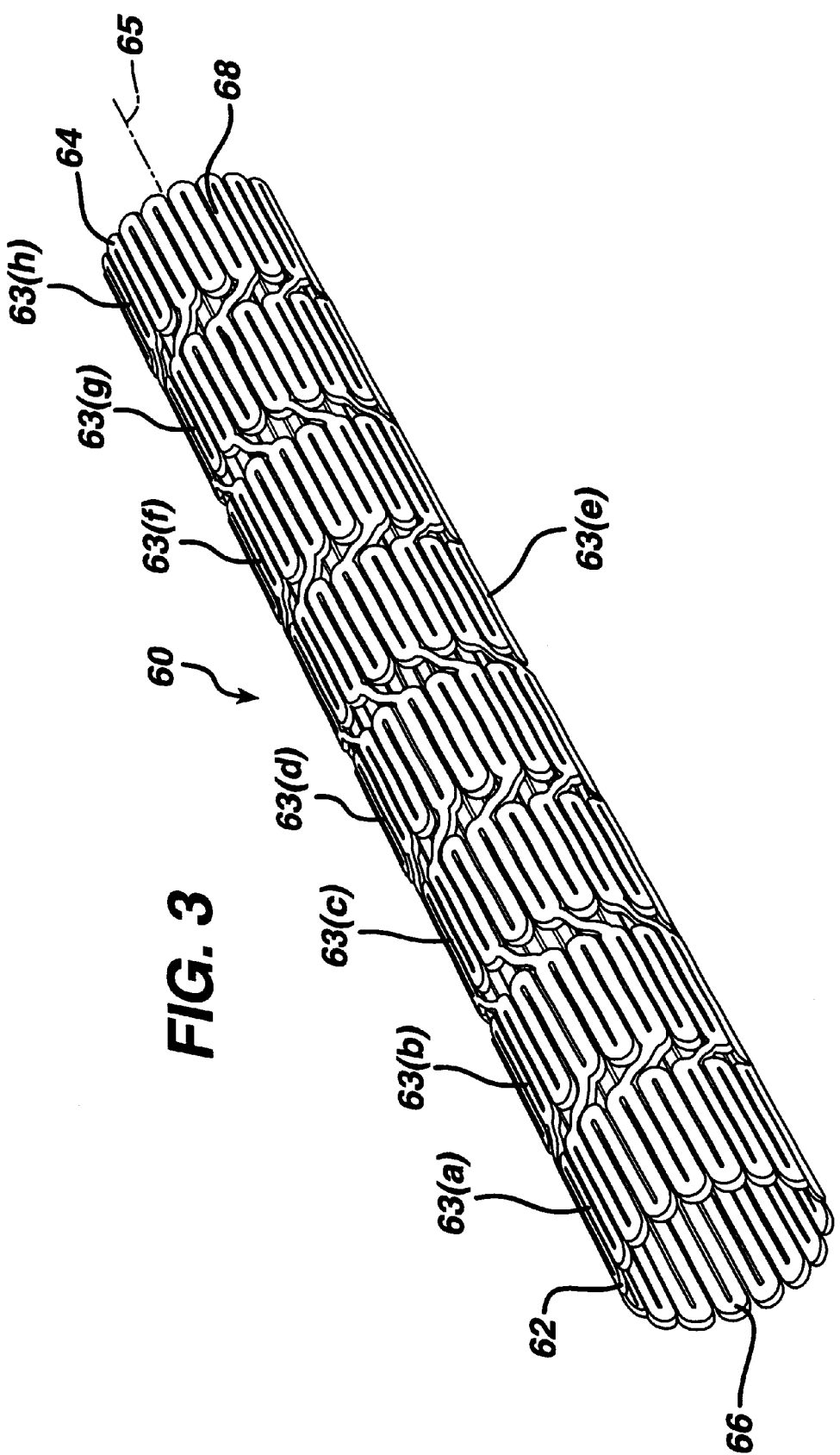
FIG. 3 is a perspective view of an inner/outer stent made in accordance with the present invention, showing the stent in its compressed state without any graft member disposed thereon.
Figure 4:
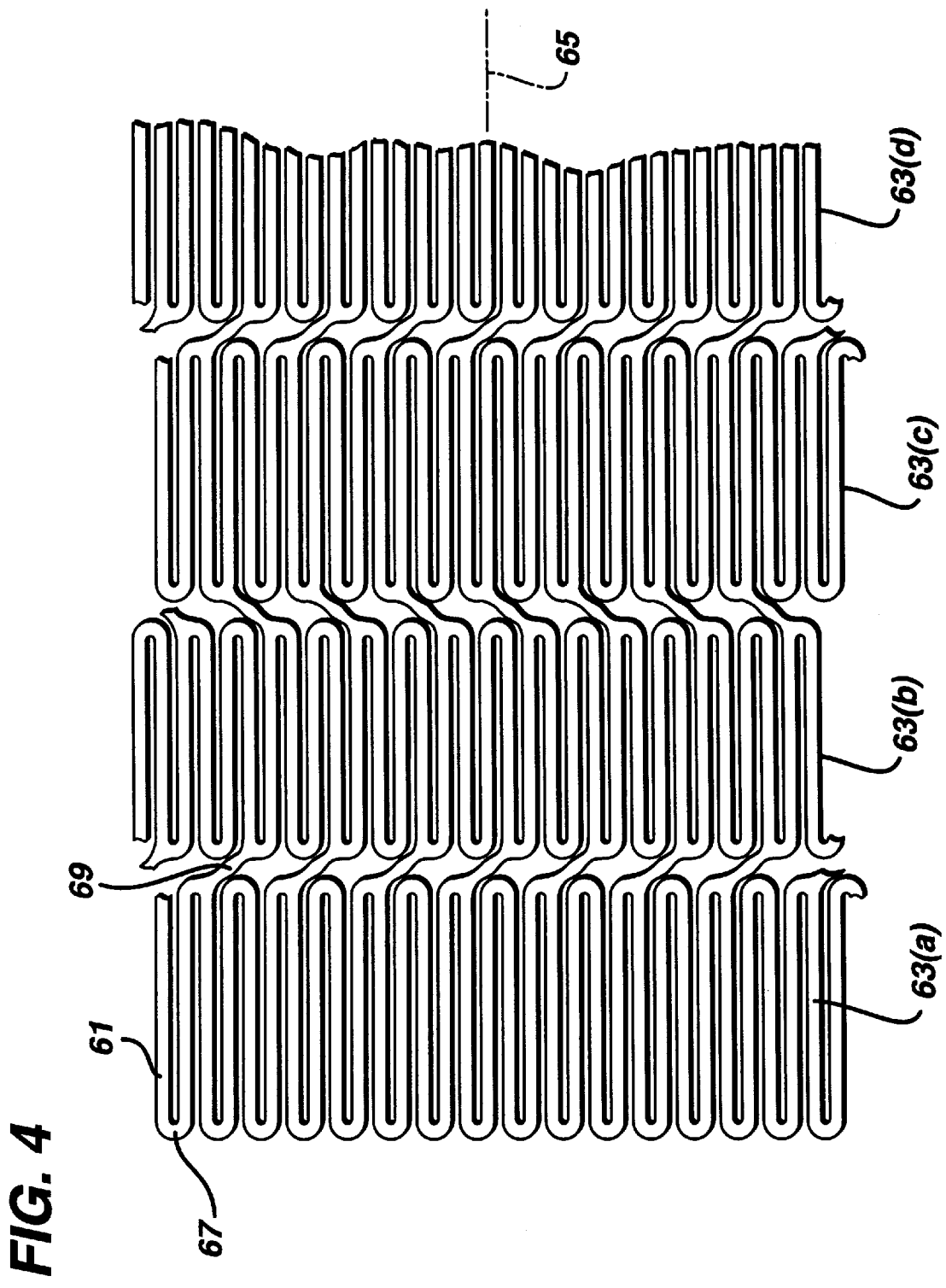
FIG. 4 is a sectional, flat view of the stent shown in FIG. 1.

Outer stent 60 and inner stent 80 are preferably substantially identical although the inner stent 80 could be longer than the outer stent 60. Therefore, a single detailed description of outer stent 60 should be sufficient to describe both stents. FIGS. 3 and 4 show stent 60 in its un-expanded or crimped state. Stent 60 is preferably made from a superelastic alloy such as Nitinol. Most preferably, stent 60 is made from an alloy comprising from about 50.5% (as used herein these percentages refer to atomic percentages) Ni to about 60% Ni, and most preferably about 55% Ni, with the remainder of the alloy Ti. Preferably, the stent is such that it is superelastic at body temperature, and preferably has an Af in the range from about 24° C. to about 37° C. The superelastic design of the stent makes it crush recoverable which, as discussed above, is useful in treating many vascular problems.

Figure 5:
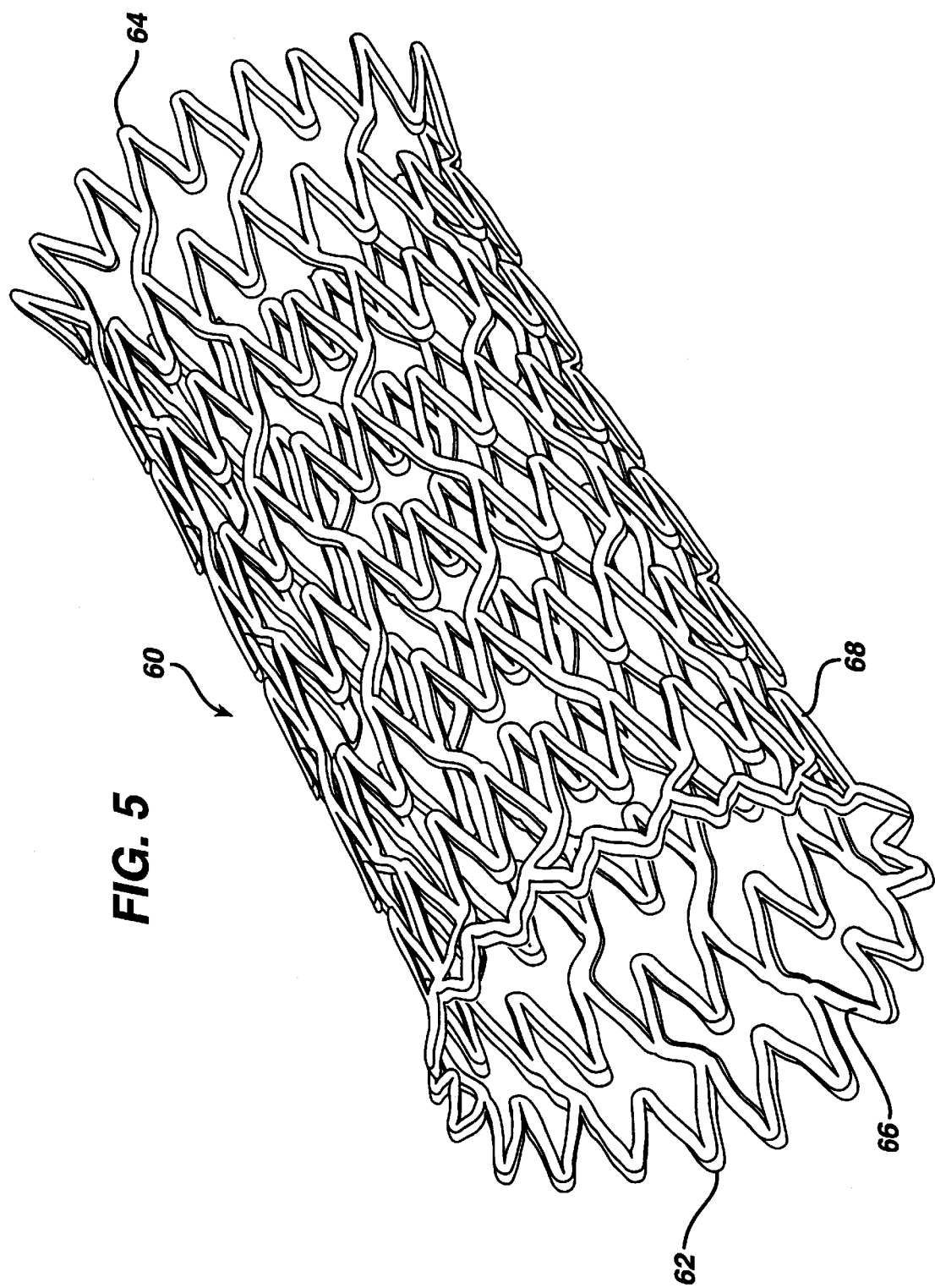
FIG. 5 is a partial perspective view of the stent shown in FIG. 1 but showing it in its expanded state.

Stent 60 is a tubular member having front and back open ends 62 and 64 and a longitudinal axis 65 extending therebetween. The tubular member has a crimped diameter, FIGS. 3 and 4, and a second larger expanded diameter, FIG. 5. The tubular member is made from a plurality of adjacent hoops 63, FIG. 3 showing hoops 63(a)–63(h), extending between the front and back ends 62 and 64. As seen from FIG. 4, the hoops 63 include a plurality of longitudinal struts 61 and a plurality of loops 67 connecting adjacent struts, wherein adjacent struts are connected at opposite ends so as to form an S shape pattern.

Stent 60 further includes a plurality of bridges 69 which connect adjacent hoops together. The bridges have one end attached to one strut and/or loop and another end attached to a strut and/or loop on an adjacent hoop. Bridges 69 connect adjacent struts together at bridge to loop connection points which are separated angularly with respect to the longitudinal axis. That is, the connection points are not immediately opposite each other. One could not draw a straight line between the connection points, wherein such line would be parallel to the longitudinal axis of the stent. Preferably, each hoop has between 24 to 36 or more struts. It has been determined that a stent having a ratio of number of struts per hoop to strut length L (in inches) which is greater than 400 has increased rigidity over prior art stents which typically have a ratio of under 200. The length of a strut is measured in its compressed state parallel to the longitudinal axis 65 of the stent.

As seen from FIGS. 3, 4, 5 and 6, the geometry of the stent changes quite significantly as a stent is deployed from its un-expanded state to its expanded state. As a stent undergoes diametric change, the strut angle and strain levels in the loops and bridges are effected. Preferably, all of the stent features will strain in a predictable manor so that the stent is reliable and uniform in strength. In addition, it is preferable to minimize the maximum strain experienced by struts loops and bridges, since Nitinol properties are more generally limited by strain rather than by stress as most materials are. In trying to minimize the maximum strain experienced by features, the present invention utilizes structural geometry's which distribute strain to areas of the stent which are less susceptible to failure than others. For example, one of the most vulnerable areas of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge connection points. One way to accomplish this is to utilize the largest possible radii while maintaining feature widths which are consistent with applied forces. Preferably, loop to bridge connection points have centers which are off set from the center of the loops to which they are attached. The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improve fatigue life by minimizing local strain levels, allows for smaller open areas which enhance entrapment of embolic material, and improves stent apposition in irregular vessel wall shapes and curves.

Preferably, loops 67 have widths, as measured at the center parallel to axis 65, which are greater than the strut widths, as measured perpendicular to axis 65. In fact, it is preferable that the thickness of the loops vary so that they are thickest near their centers This increases strain deformation at the strut and reduces the maximum strain levels at the extreme radii of the loop. This reduces the risk of stent failure and allows us to maximize radial strength properties. The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improves fatigue life by minimizing local strain levels, allows for smaller open areas which enhance entrapment of embolic material, and improves stent apposition in irregular vessel wall shapes and curves.

As mentioned above, bridge geometry changes as a stent is deployed from its compressed state to its expanded state and vise-versa. As a stent undergoes diametric change, strut angle and loop strain is effected. Since the bridges are connected to either the loops, struts or both, they are effected. Twisting of one end of the stent with respect to the other, while loaded in the stent delivery system, should be avoided. Local torque delivered to the bridge ends displaces the bridge geometry. If the bridge design is duplicated around the stent perimeter, this displacement causes rotational shifting of the two loops connected by the bridges. If the bridge design is duplicated throughout the stent, as in the present invention, this shift will occur down the length of the stent. This is a cumulative effect as one considers rotation of one end with respect to the other upon deployment. A stent delivery system, such as the one described below, will deploy the distal end first, then allow the proximal end to expand. It would be undesirable to allow the distal end to anchor into the vessel wall while holding the stent fixed in rotation, then release the proximal end. This could cause the stent to twist or whip in rotation to equilibrium after it is at least partially deployed within the vessel. Such whipping action could cause damage to the vessel.

However, one exemplary embodiment of the present invention, as shown in FIGS. 3 and 4, reduces the chance of such events from happening when deploying the stent. By mirroring the bridge geometry longitudinally down the stent, the rotational shift of the Z-sections can be made to alternate and will minimize large rotational changes between any two points on a given stent during deployment or constraint. That is, the bridges connecting loop 63(*b*) to loop 63(*c*) are angled upwardly from left to right, while the bridges connecting loop 63(*c*) to loop 63(*d*) are angled downwardly from left to right. This alternating pattern is repeated down the length of the stent. This alternating pattern of bridge slopes improves the torsional characteristics of the stent so as to minimize any twisting or rotation of the stent with respect to any two hoops. This alternating bridge slope is particularly beneficial if the stent starts to twist in vivo. As the stent twists, the diameter of the stent will change. Alternating bridge slopes tend to minimize this effect. The diameter of a stent having bridges which are all sloped in the same direction will tend grow if twisted in one direction and shrink if twisted in the other direction. With alternating bridge slopes this effect is minimized and localized.

This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improve fatigue life by minimizing local strain levels, allows for smaller open areas which enhance entrapment of embolic material, and improves stent apposition in irregular vessel wall shapes and curves.

Preferably, stents are laser cut from small diameter tubing. For prior art stents, this manufacturing process lead to designs with geometric features, such as struts, loops and bridges, having axial widths which are larger than the tube wall thickness. When the stent is compressed, most of the bending occurs in the plane that is created if one were to cut longitudinally down the stent and flatten it out. However, for the individual bridges, loops and struts, which have widths greater than their thickness, they have a greater resistance to this in-plane bending than they do to out of plane bending. Because of this, the bridges and struts tend to twist, so that the stent as a whole can bend more easily. This twisting is a buckling condition which is unpredictable and can cause potentially high strain.

However, this problem can be reduced by providing struts, hoops and bridges whose widths are equal to or less than the wall thickness of the tube. Therefore, substantially all bending and, therefore, all strains are "out of plane." This minimizes twisting of the stent which minimizes or eliminates buckling and unpredictable strain conditions. This feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improve fatigue life by minimizing local strain levels, allows for smaller open areas which enhance entrapment of embolic material, and improves stent apposition in irregular vessel wall shapes and curves.

As mentioned above, it is preferred that the stent of the present invention be made from a superelastic alloy and most preferably made of an alloy material having greater than 50.5 atomic % Nickel and the balance titanium. Greater than 50.5 atomic % Nickel allows for an alloy in which the temperature at which the martensite phase transforms completely to the austenite phase (the Af temperature) is below human body temperature and preferably is about 24° C. to about 37° C. so that austenite is the only stable phase at body temperature.

In manufacturing the Nitinol stent, the material is first in the form of a tube. Nitinol tubing is commercially available from a number of suppliers including Nitinol Devices and Components, Fremont Calif. The tubular member is then loaded into a machine which will cut the predetermined pattern of the stent, which was discussed above and is shown in the figures, into the tube. Machines for cutting patterns in tubular devices to make stents or the like are well known to those of ordinary skill in the art and are commercially available. Such machines typically hold the metal tube between the open ends while a cutting laser, preferably under microprocessor control, cuts the pattern. The pattern dimensions and styles, laser positioning requirements, and other information are programmed into a microprocessor which controls all aspects of the process. After the stent pattern is cut, the stent is treated and polished using any number of methods well known to those skilled in the art. Lastly, the stent is then cooled until it is completely martensitic.

Graft member 70 is preferably made from expanded Polytetrafluroethylene (ePTFE). Methods for making ePTFE are well known in art, and are also described in U.S. Pat. No. 4,187,390 issued to Gore on Feb. 5, 1980, which is hereby incorporated herein by reference. The porous structure of ePTFE consists of nodes interconnected by very small fibrils. Porosity for ePTFE is not measured by the diameter of a hole or pore through the sheet but is the distance from one node (internodal distance) to another among a plurality of nodes making up a pore. Expanded, porous PTFE material offers a number of advantages when used as a prosthetic vascular graft. PTFE is highly biocompatible, has excellent mechanical and handling characteristics, does not require preclotting with the patient's blood, heals relatively quickly following implantation, and is thromboresistant. In general, large pore size PTFE grafts may enhance vascular graft patency, most likely because grafts with large interstitial spaces may improve healing by possibly increasing tissue ingrowth.

Preferably, the ePTFE graft member has an average internodal distance greater than 115 microns. Larger porosity may allow for the migration of cells to facilitate a more stable neointima on the surface of the stent-graft implant. Typically, re-endothelialization of stent-grafts is minimal along the lumen surface. Cellular activity to promote healing appears to occur focally at the ends of the stent-graft which may lead to loss of patency. Larger porosity may allow for more active communication and cellular passage within the stent-graft ePTFE matrix promoting a more stable structure for long-term performance.

Figure 7:
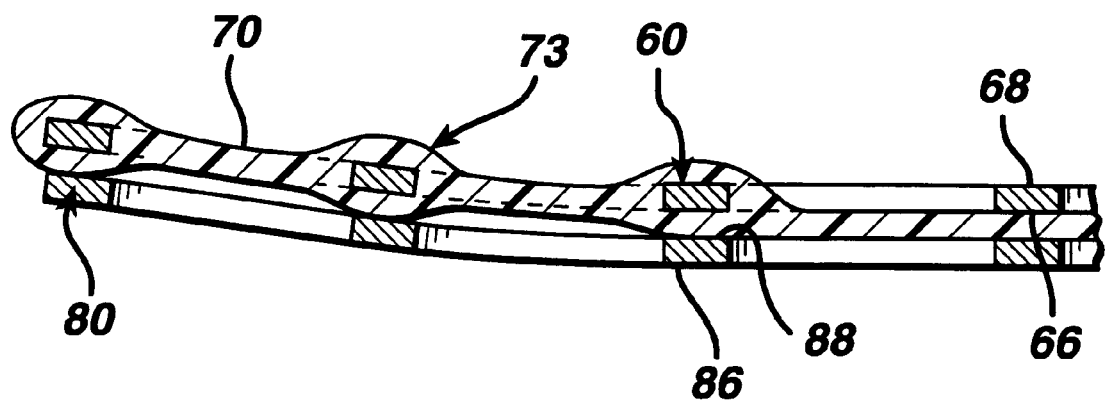
FIG. 7 is a simplified cross-sectional view of an end of the stent graft shown in FIG. 6.

As mentioned above, the cuffs 73 and 75 are bonded to the outer stent 60, preferably by the application of heat and pressure. This can best be described by referring to FIG. 7. This sealing is done when the stent 60 is in its fully expanded state. However, as will be described below, stent-graft 50 is then later crimped for delivery into the vasculature. As the stent-graft 50 is crimped, that is lowered in diameter, it will lengthen. This effect is called forelonging, and could cause the graft member 70 to tear. For prior art balloon expandable stent-grafts, the graft material was assembled with the stents, when the stents were in their crimped condition. The cuffs were not bonded to the outer stent, so as the stent was expanded, the cuffs could shorten, pulling more material into the interior of the stent-graft. This design was an attempt to prevent the graft material from tearing as the stent is expanded.

However, due to the nature of self-expanding stents, and particularly Nitinol stents, the graft material must be assembled onto the stent graft, with the outer stent in its fully expanded condition. The graft material must be assembled with the outer stent fully expanded, since the stent is deployed without the use of a balloon to expand the stent and the graft material. Typically with balloon expandable stent-grafts, the graft material is assembled on to the stent with the stent in a crimped condition. The graft material is the same approximate diameter as the crimped stent and both are expanded to the desired diameter by inflating the balloon. With a self-expanding stent-graft, both the stent and the graft material must expand to its rated diameter in order to make apposition with the vessel without the use of a balloon. If the stent-graft does not fully expand then the stent-graft could float in the vasculature and not anchor at the desired location. In addition, it has been found that their are many advantages to bonding the ends of the graft member onto the outer stent. The first advantage is during the manufacturing process, where having the graft bonded to the outer stent insures that the PTFE material will not move as the stent-graft is assembled and crimped. Secondly, as the crimped stent-graft is transferred from the split hypotube (discussed below) to the transfer tube and finally into the delivery system the bonded areas help to prevent the graft material from folding back and coming off the stent. Lastly, as the stent-graft is deployed the bonded areas help maintain the graft material folded over and secured on to the outer stent to prevent the ePTFE from coming off and draping into the vessel lumen.

It has been discovered herein that the problem of forelonging can be solved by making the length of the stent graft along the interior surface of stent 60 longer than stent 60, as measured along its longitudinal axis. That is there will be slack in the graft material when it is in its fully expanded state. Preferably, the length of the graft material along the interior surface of stent 60 is from 3–10% larger, depending on the expanded diameter of the outer stent. Larger stents will forelong more, while smaller stents will forelong less. This extra material allows the graft material to forelong, while reducing the chances of tearing.

Figure 8:
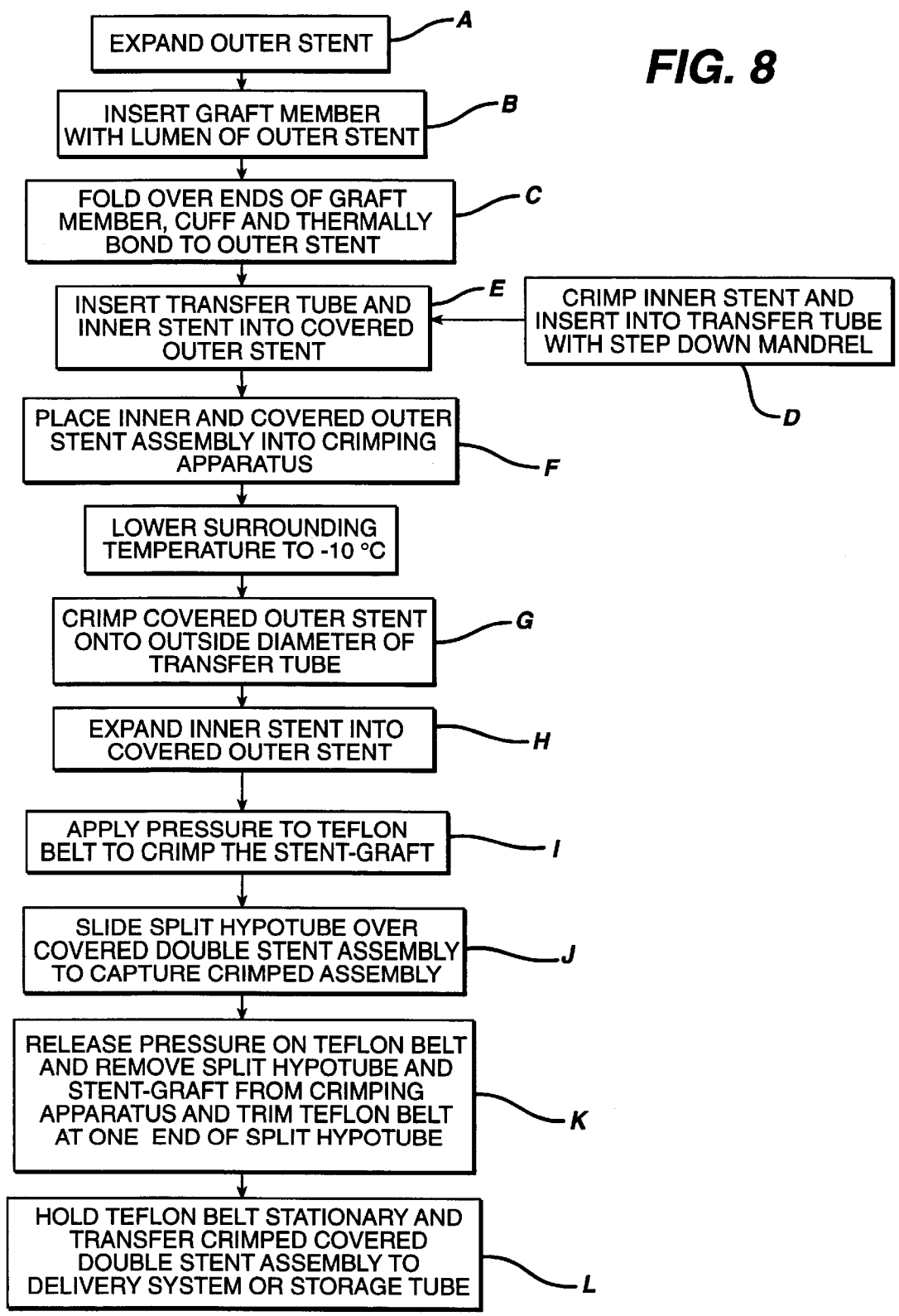
FIG. 8 is a schematic drawing showing the steps in the manufacture of a stent-graft made in accordance with the present invention.
Figure 9F:
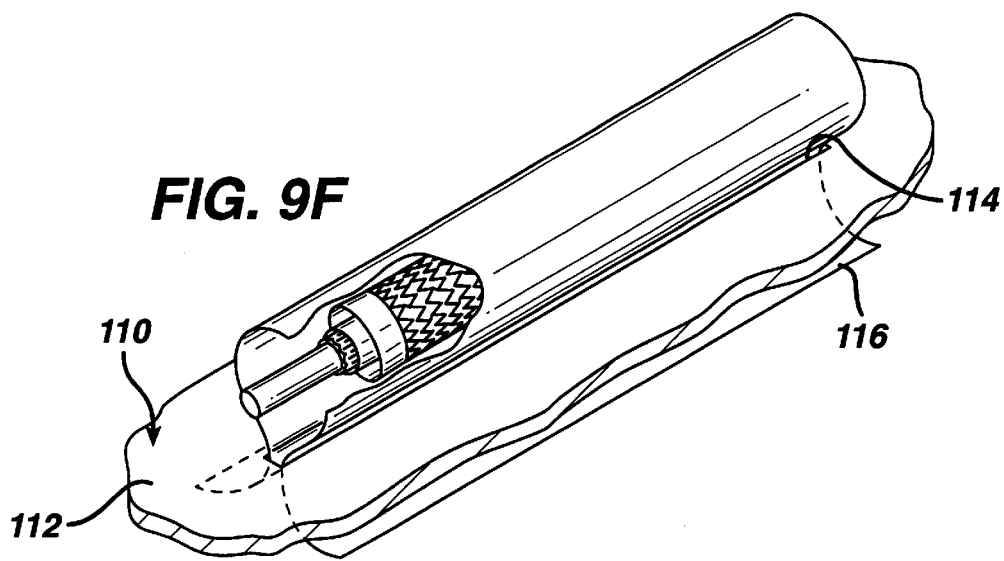
Figure 9G:
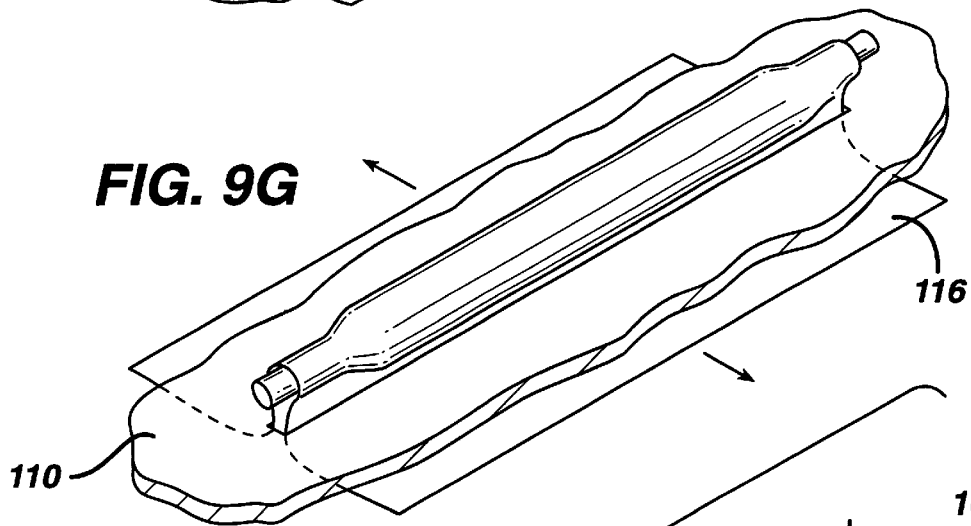
Figure 9H:
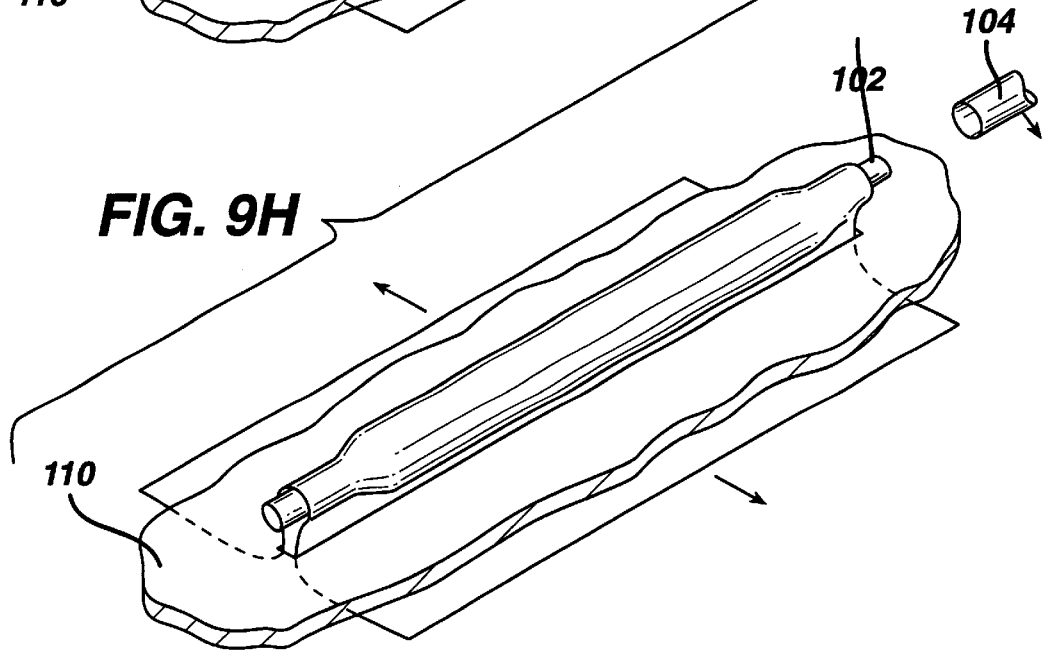
Figure 9I:
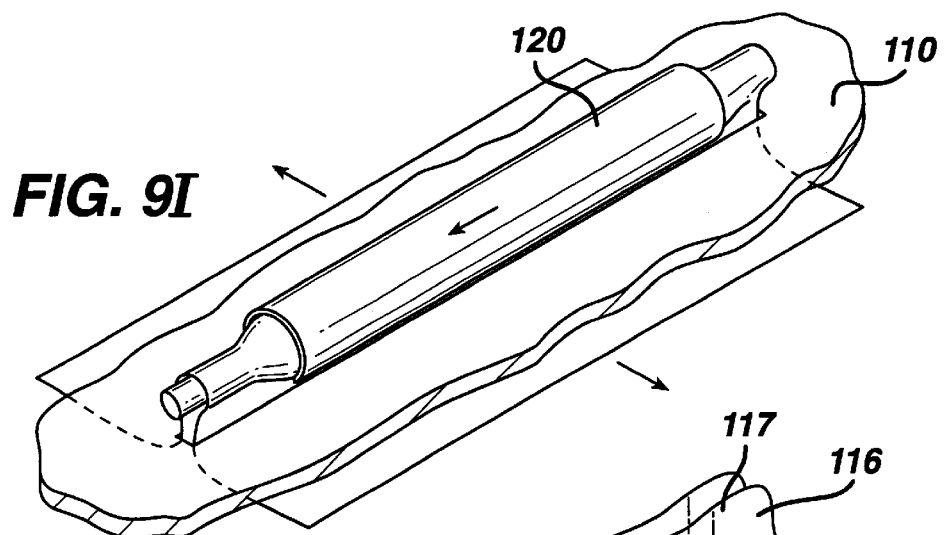
Figure 9J:
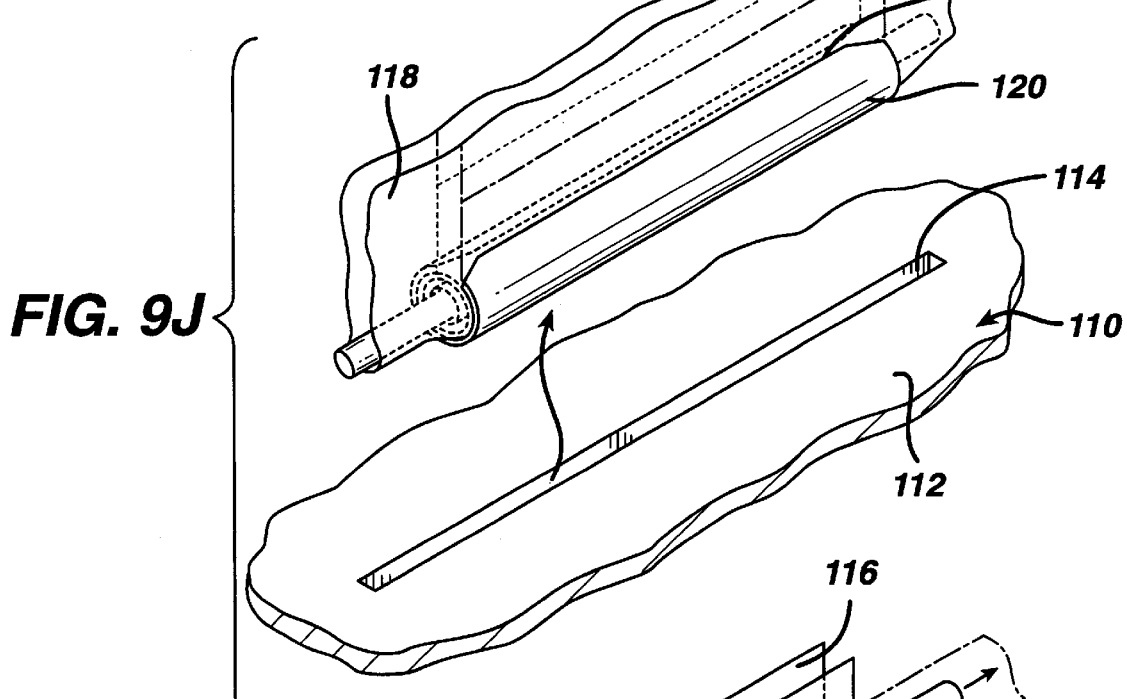
Figure 9K:
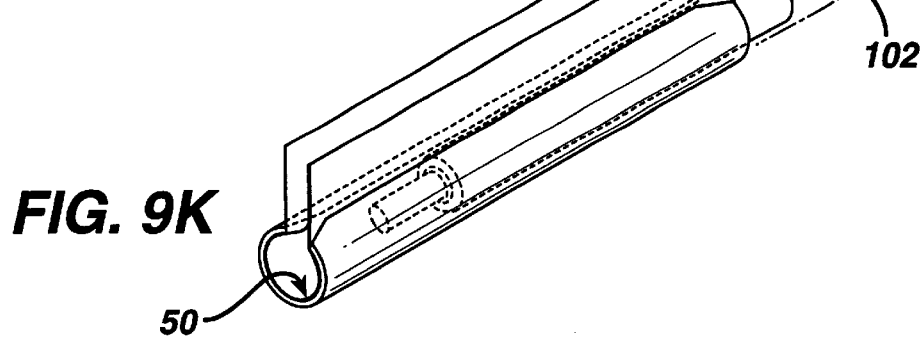
Figure 10A:
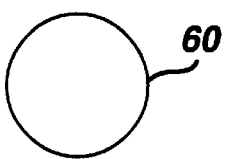
FIGS. 10A–10K are axial cross-sectional views of FIGS. 9A–9K respectively.
Figure 10B:
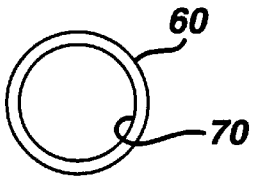
Figure 10C:
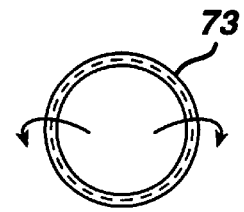
Figure 10D:
Figure 10E:
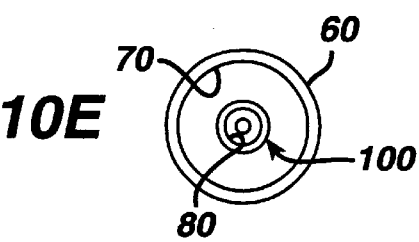
Figure 10F:
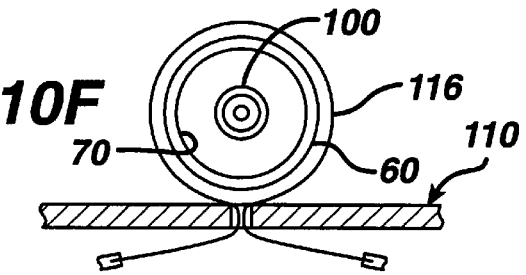
Figure 10G:
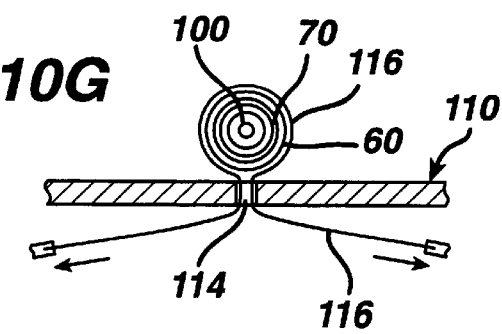
Figure 10H:
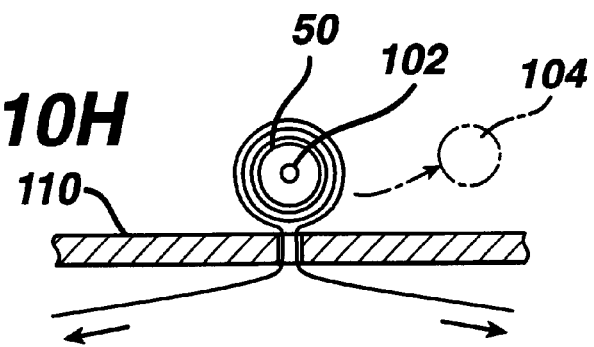
Figure 10I:
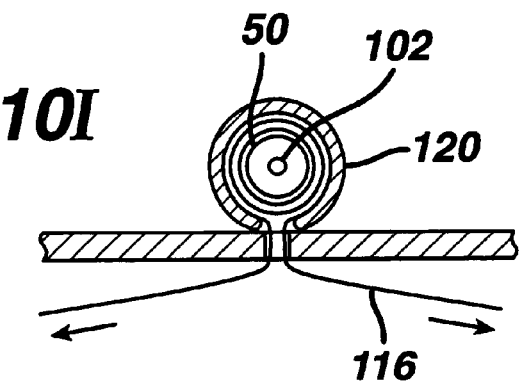
Figure 10J:
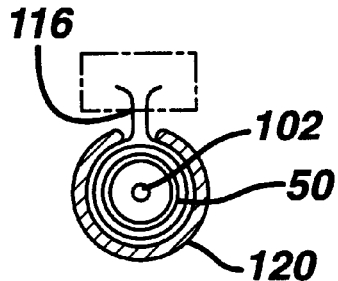
Figure 10K:
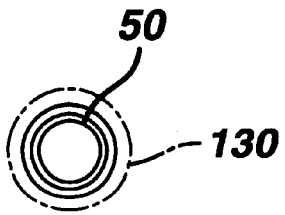

By referring to FIG. 8, in conjunction with FIGS. 9A–K and 10A–K, one can better understand how stent-graft 50 is manufactured. Outer stent 60 is allowed to fully expand. Thereafter, graft member 70 is inserted into the interior or lumen of stent 69, and the front and back ends 72 and 74 of the graft member 70 are folded back onto stent 60 to form cuffs 73 and 75. Heat and pressure are then applied to cuffs 73 and 75, so that the graft is now attached to the front and back ends 62 and 64 of stent 60. Stent 80 is put in its crimped state and loaded into a transfer tube 100. Transfer tube 100, in many ways, is similar to the delivery device for stent-graft 50, which is discussed in detail below. Transfer tube 100 has an inner shaft 102 and an outer sheath 104. Transfer tube 100, having crimped stent 80 loaded therein, is then placed in the interior or lumen of the graft member 70 forming assembly 106.

Assembly 106 is then placed onto crimping apparatus 110. Crimping apparatus 110 comprises a rigid member 112 having a slit 114 therein, and a PTFE belt 116. Assembly 106 is disposed on apparatus 110 such that belt 116 wraps around it, with the ends of the belt extending through slit 114. The temperature of the manufacturing room is then lowered such that the Nitinol stents 60 and 80 are in a fully martensitic condition, which aids in the crimping of outer stent 60. Preferably the room is lowered to about −10° C. Belt 116 is then pulled at its ends until stent 60 is in its crimped state and graft member 70 abuts against transfer tube 100. Thereafter, the outer sheath 104 of transfer tube 100 is removed, such that inner stent 80 is deployed within graft member 70 and inner stent 60, forming stent-graft 50. Hypo tube 120, having a slit 122 therein, is then slid over the belt 116. The pressure on belt 116 is released, and end 117 of the belt is trimmed off, and inner shaft 102 is removed. If the belt is removed, the crimped stent graft would come out with the belt, and it is better to have the stent-graft in contact with PTFE (lubricious) surface rather than the inside of the metallic split hypotube. Thereafter, the stent-graft 50 can be transferred to a storage tube 130 (shown in FIG. 10K), or placed within the delivery device, using any method well known to those skilled in the art. Transferring the crimped stent-graft from the split hypotube into the transfer tube or into the delivery system is a similar process. The crimping mandrel is removed and replaced by a transfer mandrel (larger diameter at the proximal end), which is used to push the stent-graft into the transfer tube or the delivery system.

Figure 1:
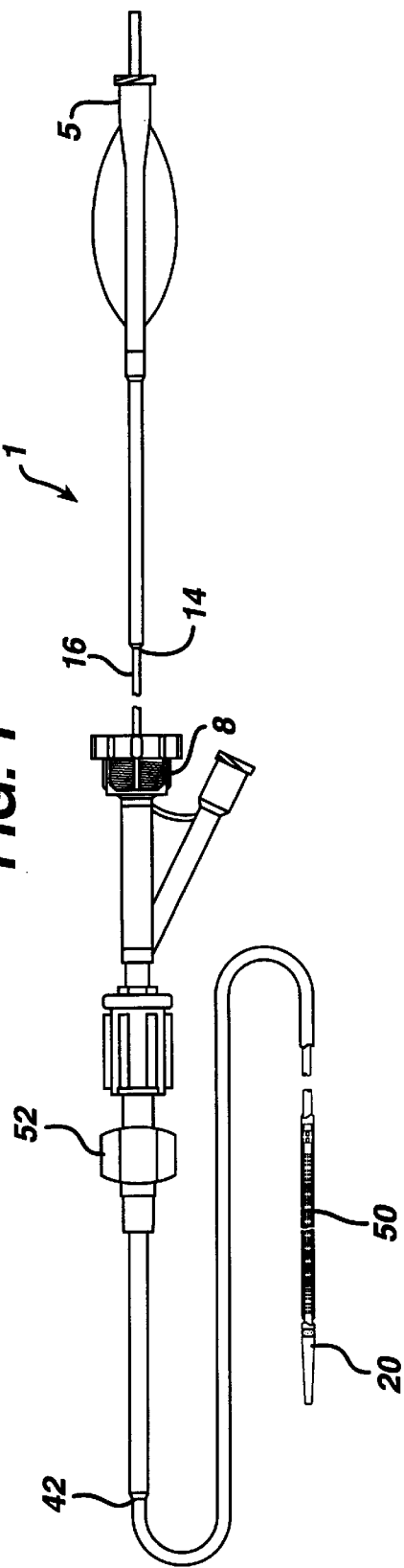
FIG. 1 is a simplified partial cross-sectional view of a stent delivery apparatus having a stent loaded therein, which can be used with a stent-graft made in accordance with the present invention.
Figure 2:
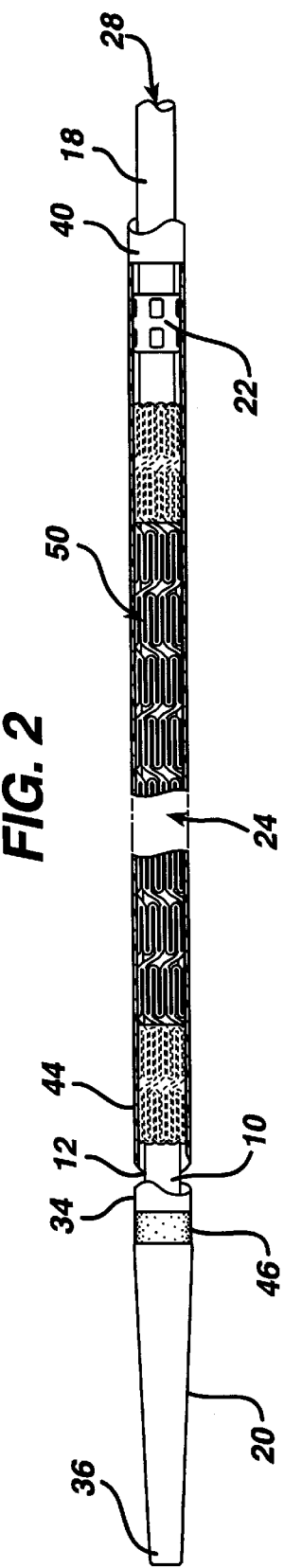
FIG. 2 is a view similar to that of FIG. 1 but showing an enlarged view of the distal end of the apparatus.

It is believed that many of the advantages of the present invention can be better understood through a brief description of a delivery apparatus for the stent, as shown in FIGS. 1 and 2. FIGS. 1 and 2 show a self-expanding stent delivery apparatus 1 for a stent made in accordance with the present invention. Apparatus 1 comprises inner and outer coaxial tubes. The inner tube is called the shaft 10 and the outer tube is called the sheath 40. Shaft 10 has proximal and distal ends 12 and 14 respectively. The distal end 14 of the shaft terminates at a luer lock hub 5. Preferably, shaft 10 has a proximal portion 16 which is made from a relatively stiff material such as stainless steel, Nitinol, or any other suitable material, and distal portion 18 which is made from a polyethylene, polyimide, pellethane, Pebax, Vestamid, Cristamid, Grillamid or any other suitable material known to those of ordinary skill in the art. The two portions are joined together by any number of means known to those of ordinary skill in the art. The stainless steel proximal end gives the shaft the necessary rigidity or stiffness it needs to effectively push out the stent, while the polymeric distal portion provides the necessary flexibility to navigate tortuous vessels.

The distal portion 18 of the shaft has a distal tip 20 attached thereto. The distal tip 20 has a proximal end 34 whose diameter is substantially the same as the outer diameter of the sheath 40. The distal tip tapers to a smaller diameter from its proximal end to its distal end, wherein the distal end 36 of the distal tip has a diameter smaller than the inner diameter of the sheath. Also attached to distal portion 18 of shaft 10 is a stop 22 which is proximal to the distal tip 20. Stop 22 can be made from any number of materials known in the art, including stainless steel, and is even more preferably made from a highly radiopaque material such as platinum, gold tantalum. The diameter of stop 22 is substantially the same as the inner diameter of sheath 40, and would actually make frictional contact with the inner surface of the sheath. Stop 22 helps to push the stent-graft out of the sheath during deployment, and helps the stent-graft from migrating proximally into the sheath 40.

A stent bed 24 is defined as being that portion of the shaft between the distal tip 20 and the stop 22. The stent bed 24 and the stent-graft 50 are coaxial so that the portion of shaft 18 comprising the stent bed 24 is located within the lumen of the stent-graft 50. However, the stent bed 24 does not make any contact with stent-graft 50 itself. Lastly, shaft 10 has a guidewire lumen 28 extending along its length from its proximal end 12 and exiting through its distal tip 20. This allows the shaft 10 to receive a guidewire much in the same way that an ordinary balloon angioplastly catheter receives a guidewire. Such guidewires are well known in art and help guide catheters and other medical devices through the vasculature of the body.

Sheath 40 is preferably a polymeric catheter and has a proximal end 42 terminating at a hub 52. Sheath 40 also has a distal end 44 which terminates at the proximal end 34 of distal tip 20 of the shaft 18, when the stent-graft is in its fully un-deployed position as shown in the figures. The distal end 44 of sheath 40 includes a radiopaque marker band 46 disposed along its outer surface. As will be explained below, the stent-graft is fully deployed when the marker band 46 is lined up with radiopaque stop 22, thus indicating to the physician that it is now safe to remove the apparatus 1 from the body. Sheath 40 preferably comprises an outer polymeric layer and an inner polymeric layer. Positioned between the outer and inner layers a braided reinforcing layer. Braided reinforcing layer is preferably made from stainless steel. The use of braided reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

FIGS. 1 and 2 show the stent-graft 50 as being in its fully un-deployed position. This is the position the stent-graft 50 is in when the apparatus 1 is inserted into the vasculature and its distal end is navigated to a target site. Stent-graft 50 is disposed around stent bed 24 and at the distal end 44 of sheath 40. The distal tip 20 of the shaft 10 is distal to the distal end 44 of the sheath 40, and the proximal end 12 of the shaft 10 is proximal to the proximal end 42 of the sheath 40. The stent-graft 50 is in a compressed state and makes frictional contact with the inner surface 48 of the sheath 40.

When being inserted into a patient, sheath 40 and shaft 10 are locked together at their proximal ends by a Tuohy Borst valve 8. This prevents any sliding movement between the shaft and sheath which could result in a premature deployment or partial deployment of the stent-graft. When the stent-graft 50 reaches its target site and is ready for deployment, the Tuohy Borst valve 8 is opened so that that the sheath 40 and shaft 10 are no longer locked together.

The method under which apparatus 1 deploys stent-graft 50 should be readily apparent. The apparatus 1 is first inserted into a vessel so that the stent bed 24 is at a target diseased site. Once this has occurred the physician would open the Tuohy Borst valve 8. The physician would then grasp the proximal end 12 of shaft 10 so as to hold it in place. Thereafter, the physician would grasp the proximal end 42 of sheath 40 and slide it proximal, relative to the shaft 40. Stop 22 prevents the stent-graft 50 from sliding back with the sheath 40, so that as the sheath 40 is moved back, the stent-graft 50 is pushed out of the distal end 44 of the sheath 40. Stent-graft deployment is complete when the radiopaque band 46 on the sheath 40 is proximal to radiopaque stop 22. The apparatus 1 can now be withdrawn through stent-graft 50 and removed from the patient.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A method of making a stent-graft for insertion into target site within a vessel of a patient, said graft having a crimped state for delivery to said target site, and an expanded state for implantation therein, said method comprising the steps of:
   a) providing a self-expanding tubular elastic outer stent having a crimped and expanded state, and expanding said outer stent to its expanded state;
   b) providing a tubular flexible porous graft member and inserting said graft member along an interior of said outer stent; and
   c) providing a self-expanding tubular elastic inner stent and crimping said outer stent to a diameter smaller than a diameter of said expanded outer stent, inserting said inner stent within an interior of said graft member, and expanding said inner stent such that said inner stent, said graft member and said outer stent are all abutting.

2. The method according to claim 1 further including the step of attaching said graft member to said outer stent.

3. The method according to claim 2 wherein said graft member has front and back ends which extend beyond a front and back end of said outer stent, and wherein said step of attaching said graft member to said outer stent comprises folding said front and back ends of said graft member over said front and back ends of said outer stent to form cuffs.

4. The method according to claim 3 further including the step of applying heat and pressure to said cuffs.

5. The stent graft according to claim 1 wherein said inner and outer stents are made from a nickel titanium alloy which exhibits superelastic properties at body temperature.

6. The stent-graft according to claim 2 wherein said alloy comprises from about 50.5 percent to about 60 percent Nickel and the remainder comprising Titanium.

7. The stent-graft according to claim 1, wherein said graft member comprises expanded polytetrafluroethylene which forms nodes interconnected by fibrils.

8. The stent graft according to claim 7, wherein the average said graft member has an average internodal distance greater than 100 microns.

9. A method of making a stent-graft for insertion into target site within a vessel of a patient, said graft having a crimped state for delivery to said target site, and an expanded state for implantation therein, said method comprising the steps of;
   a) providing a self-expanding tubular elastic outer stent having a crimped and expanded state and front and back ends, and expanding said outer stent to its expanded state;

b) providing a tubular flexible porous graft member having front and back ends, and inserting said graft member along an interior of said outer stent, wherein afterwhich a length of said graft member which is disposed along said interior of said outer stent between its front and back ends that is greater than a length of said outer stent between its front and back ends, whereby there is slack in said graft member; and c) providing a self-expanding tubular elastic inner stent and crimping said outer stent to a diameter smaller than a diameter of said expanded outer stent, inserting said inner stent within an interior of said graft member, and expanding said inner stent such that said inner stent, said graft member and said outer stent are all abutting.

10. The method according to claim 9 further including the step of attaching said graft member to said outer stent.

11. The method according to claim 10 wherein the step of attaching said graft member to said outer stent comprises the step of attaching said graft member to said outer stent at said outer stent's front and back ends.

12. The method according to claim 11 wherein said step of attaching said graft member to said outer stent comprises folding said front and back ends of said graft member over said front and back ends of said outer stent to form cuffs.

13. The method according to claim 12 further including the step of applying heat and pressure to said cuffs.

14. The stent graft according to claim 9 wherein said inner and outer stents are made from a nickel titanium alloy which exhibits superelastic properties at body temperature.

15. The stent-graft according to claim 14 wherein said alloy comprises from about 50.5 percent to about 60 percent Nickel and the remainder comprising Titanium.

16. The stent-graft according to claim 9, wherein said graft member comprises expanded polytetrafluroethylene which forms nodes interconnected by fibrils.

17. The stent graft according to claim 16, wherein the average said graft member has an average internodal distance greater than 100 microns.

18. A method of making a stent-graft for insertion into target site within a vessel of a patient, said graft having a crimped state for delivery to said target site, and an expanded state for implantation therein, said method comprising the steps of:

a) providing a self-expanding tubular elastic outer stent having a crimped and expanded state and front and back ends, and expanding said outer stent to its expanded state;

b) providing a tubular flexible porous graft member having front and back ends, and inserting said graft member along an interior of said outer stent, folding said front and back ends of said graft member over and onto to said front and back ends of said outer stent to form cuffs, wherein afterwhich a length of said graft member which is disposed along said interior of said outer stent between its front and back ends that is greater than a length of said outer stent between its front and back ends, whereby there is slack in said graft member; and c) providing a self-expanding tubular elastic inner stent and crimping said outer stent to a diameter smaller than a diameter of said expanded outer stent, inserting said inner stent within an interior of said graft member, and expanding said inner stent such that said inner stent, said graft member and said outer stent are all abutting.

19. The method according to claim 18 further including the step of applying heat and pressure to said cuffs.

20. The stent graft according to claim 18 wherein said inner and outer stents are made from a nickel titanium alloy which exhibits superelastic properties at body temperature.

21. The stent-graft according to claim 20 wherein said alloy comprises from about 50.5 percent to about 60 percent Nickel and the remainder comprising Titanium.

22. The stent-graft according to claim 18, wherein said graft member comprises expanded polytetrafluroethylene which forms nodes interconnected by fibrils.

23. The stent graft according to claim 22, wherein the average said graft member has an average internodal distance greater than 100 microns.

24. The stent-graft of claim 18 wherein the step of attaching said graft member to said outer stent results in said length of said graft member disposed along said interior of said outer stent between its front and back ends which is 3% to 10% greater than said length of said outer stent between its front and back ends.

* * * * *